(12) United States Patent
Surma

(10) Patent No.: US 8,337,504 B2
(45) Date of Patent: Dec. 25, 2012

(54) SYSTEM AND METHOD FOR INSERTING AN IMPLANT

(75) Inventor: Gabriel Surma, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 12/879,778

(22) Filed: Sep. 10, 2010

(65) Prior Publication Data

US 2010/0331994 A1 Dec. 30, 2010

Related U.S. Application Data

(63) Continuation of application No. 11/421,972, filed on Jun. 2, 2006, now abandoned.

(51) Int. Cl.
*A61F 2/46* (2006.01)
*A61B 17/58* (2006.01)
*A61B 17/60* (2006.01)
*A61F 2/00* (2006.01)
*A61F 2/36* (2006.01)

(52) U.S. Cl. ............ 606/99; 606/86 R; 623/22.4

(58) Field of Classification Search ........... 606/99, 606/86 R; 623/22.4, 20.36
See application file for complete search history.

(56) References Cited

U.S. PATENT DOCUMENTS

| | | | |
|---|---|---|---|
| 5,409,492 A | 4/1995 | Jones | |
| 5,443,471 A | 8/1995 | Swajger | |
| 5,531,750 A * | 7/1996 | Even-Esh | ............ 606/79 |
| 5,534,006 A | 7/1996 | Szabo | |
| 5,720,750 A | 2/1998 | Koller | |
| 6,205,884 B1 | 3/2001 | Foley | |
| 6,395,004 B1 | 5/2002 | Dye | |
| 6,626,913 B1 | 9/2003 | McKinnon | |
| 7,494,509 B1 * | 2/2009 | Hershberger et al. | ....... 623/23.35 |
| 2003/0233100 A1 | 12/2003 | Santarella | |
| 2005/0177172 A1 | 8/2005 | Acker | |
| 2005/0203535 A1 | 9/2005 | Parry | |
| 2006/0015123 A1 * | 1/2006 | Fencl et al. | ............ 606/104 |
| 2006/0036264 A1 | 2/2006 | Selover | |
| 2006/0064109 A1 | 3/2006 | Iversen | |

FOREIGN PATENT DOCUMENTS

| | | |
|---|---|---|
| EP | 450007 A1 | 10/1991 |
| FR | 2615097 A1 | 11/1988 |
| FR | 2749501 A1 | 12/1997 |

OTHER PUBLICATIONS

U.S. Appl. No. 11/421,972, Non Final Rejection, Dec. 26, 2008.
U.S. Appl. No. 11/421,972, Non Final Rejection, Dec. 4, 2009.
U.S. Appl. No. 11/421,972, Final Rejection, Jun. 23, 2009.
U.S. Appl. No. 11/421,972, Final Rejection, Jun. 10, 2010.
Learmonth, Ian D.; Conservative Hip Implants; Current Orthopaedics; (2005) 255-262, vol. 19, Elsevier, www.elsevier.com/locate/cuor.

(Continued)

*Primary Examiner* — Kevin T Truong
*Assistant Examiner* — David Bates

(57) ABSTRACT

An implant includes a body configured to be implanted at least partially within a bone canal. The body has a proximal end, a longitudinal axis and a cavity located at the proximal end. The cavity is configured to mate with an insertion tool and defines a cavity axis that is not parallel to the longitudinal axis of the implant.

10 Claims, 3 Drawing Sheets

OTHER PUBLICATIONS

Santori, F.S. et al; Ultra-Short Stems with Proximal Load Transfer: Clinical and Radiographic Results at Five-year Follow-up; Hip International/vol. 15 No. 1 (suppl3) pp. S31-39; Wichtig Editore, 2006.

Walker, Peter S., et al; Design Rationale and Dimensional Considerations for a Femoral Neck Prosthesis; Clinical Orthopaedics and Related Research; Dec. 2005; pp. 313-319; No. 441, © 2005 Lippincott Williams & Wilkins.

* cited by examiner

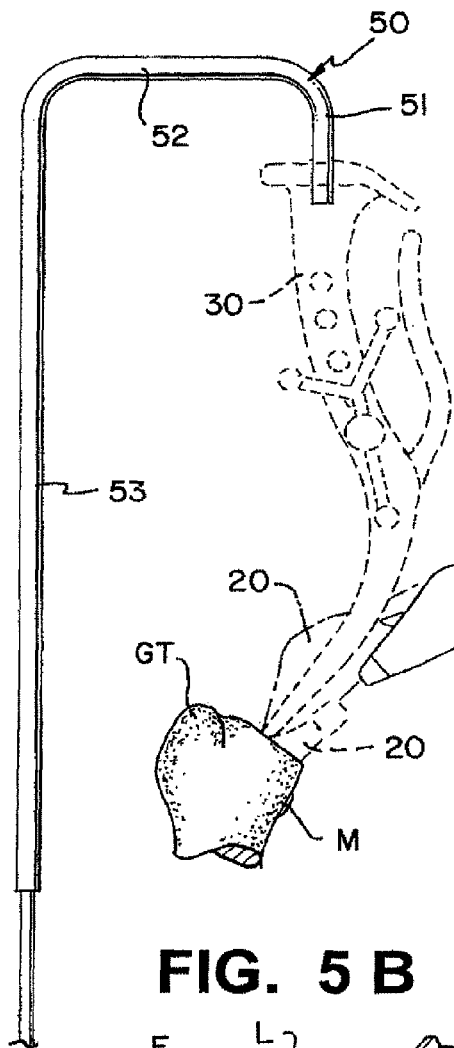
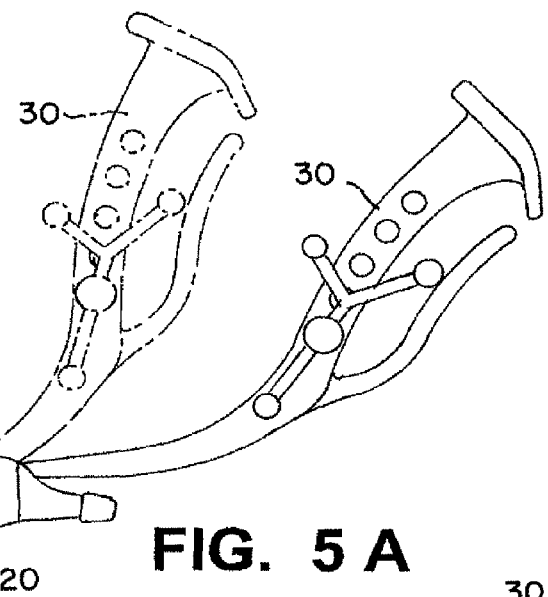
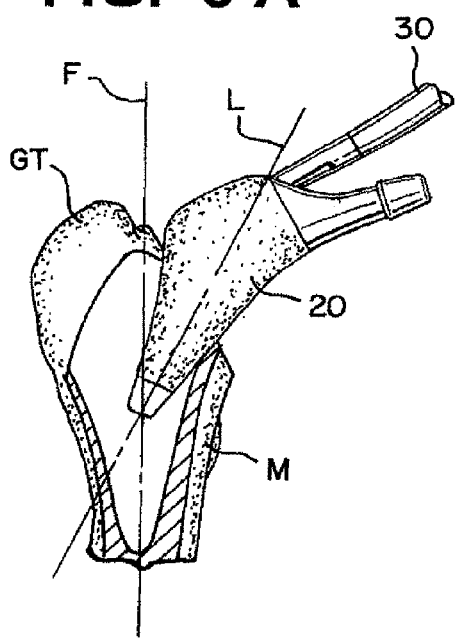
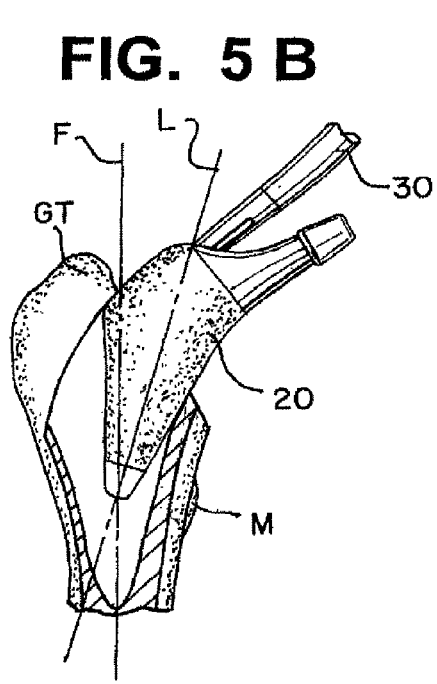
FIG. 4
FIG. 5 A
FIG. 5 B

SYSTEM AND METHOD FOR INSERTING AN IMPLANT

This invention relates to a method of and system for implanting an implant, more particularly implanting a hip implant at least partially within the femoral canal.

Orthopaedic surgeons, as with other specialties, have been driven to perform their surgery through smaller and smaller incisions in an attempt to minimize damage to tissue that surrounds the surgical site, to thereby decrease blood loss and recovery time. In orthopaedics, particularly, it is recognized that sparing a patient's bone is preferred whenever possible during surgery. In hip replacement surgery, a surgeon can attempt to spare the upper part of the femur (greater trochanter) by using a small incision surgical technique that employs a short hip implant.

An issue that occurs during this surgery is the difficulty in using an insertion feature of the implant that is positioned on the lateral-superior aspect of the implant. The feature is located at this position due to the compromise between accessibility of the feature and the mechanical strength requirements imposed on the implant. Currently available straight, in-line impactors and implant insertion features are positioned coincident with or parallel to the long (or longitudinal) axis of the implant. When the surgeon attempts to finally seat the implant using the insertion feature, the position of the insertion feature can cause the impactor to interfere with the mass of the greater trochanter. As a result of this difficulty, the surgeon may not completely seat the implant, thereby compromising the biomechanics of the joint space and potentially leading to implant subsidence and/or dislocation.

BRIEF SUMMARY OF THE INVENTION

The present invention addresses the shortcomings of the prior art by providing an improved method of and system for inserting and impacting an implant.

The preferred embodiment of the implant system allows the insertion of a short implant using the 'around the corner' surgical technique. This technique aims to minimize the damage to the greater trochanter by broaching around the medial curve of the femur and under the greater trochanter. The insertion feature located on the implant is designed to mate with the inserter/impactor tool in a way that allows for rotational control of the implant but is also removable using a low force. The system addresses the problem of greater trochanter impingement by both angling the insertion feature with respect to the long axis of the implant and curving the impactor to travel around the greater trochanter during the "around the corner" insertion motion.

While the issue of navigating a short implant in a hip procedure is described in some detail below, it is contemplated that the implant system can be used in any method where an implant needs to be inserted or positioned in a non-axial fashion. For example, a similar method and system can be used to implant humeral implants. The invention is also not necessarily limited to implantation of long-bone implants. The system can be employed wherever the insertion path of the implant benefits from being out of axis of the ultimate location of the implant.

According to the present invention a short hip implant includes a body configured to be implanted at least partially within the femoral canal. The body has a proximal end, a longitudinal axis and a cavity located at the proximal end. The cavity is configured to mate with an insertion tool, and defines a cavity axis that is not parallel to the longitudinal axis of the implant.

According to another aspect of the present invention a hip implant system includes a short hip implant having a body with a proximal end, a longitudinal axis, and a cavity. The cavity has a cavity axis that is not parallel to the longitudinal axis. The system also includes a tool for assisting in the implantation of the implant that has a distal end configured to mate with the cavity.

According to another aspect of the present invention a hip implant system includes a short hip implant having a body with a proximal end, a longitudinal axis, and a cavity. The system also includes a tool for assisting in the implantation of the implant that has a distal end configured to mate with the cavity. The distal end has an axis that is not parallel to the longitudinal axis of the body when the tool is mated with the implant.

A method of implanting a short implant at least partially within a bone, wherein the bone has an axis, is also provided. The method includes the steps of (a) providing a system including an implant having a body with a proximal end, a distal end, a longitudinal axis and a cavity located at the proximal end, the cavity being configured to mate with an insertion tool and defining a cavity axis that is not parallel to the longitudinal axis of the implant, and a tool for assisting in the implantation of the implant, the tool including a shaft having a distal end configured to mate with the cavity and a proximal end, the proximal end including a strike plate attached thereto; (b) creating a void in the bone; (c) introducing the distal end of the short implant into the void, whereat the longitudinal axis of the implant is not aligned with the bone axis; (d) engaging the distal end of the tool into the cavity of the implant; (e) striking the strike plate to thereby rotate the longitudinal axis of the implant toward the bone axis until the longitudinal axis of the implant is substantially aligned with the bone axis; and (f) disengaging the distal end of the tool from the cavity of the implant.

A method of implanting an implant at least partially within tissue, wherein the tissue includes an implant target position having a target axis and a tissue feature that intersects the target axis, is also provided. The method includes the steps of (a) providing a system including an implant that has (i) a body, the body having a proximal end, a distal end, a longitudinal axis and a cavity located at the proximal end, wherein the cavity defines a cavity axis that is not parallel to the longitudinal axis of the implant, and (ii) a tool for assisting in the implantation of the implant comprising a shaft having a distal end configured to mate with the cavity and a proximal end; (b) creating a pathway from a tissue surface to a target position within the tissue; (c) inserting the distal end of the implant into the pathway; (d) engaging the distal end of the tool with the cavity of the implant; (e) manipulating the tool to move the implant to the target position without impinging on the tissue feature; and (f) disengaging the distal end of the tool from the cavity of the implant.

BRIEF DESCRIPTION OF THE DRAWINGS

These and other features, advantages and benefits will be made apparent through the following descriptions and accompanying figures, where like reference numerals refer to the same features across the various drawings.

FIG. 4 shows a schematic view of the implant being inserted into the femur in three stages according to one embodiment of the invention.

DETAILED DESCRIPTION OF THE INVENTION

Figure 1:
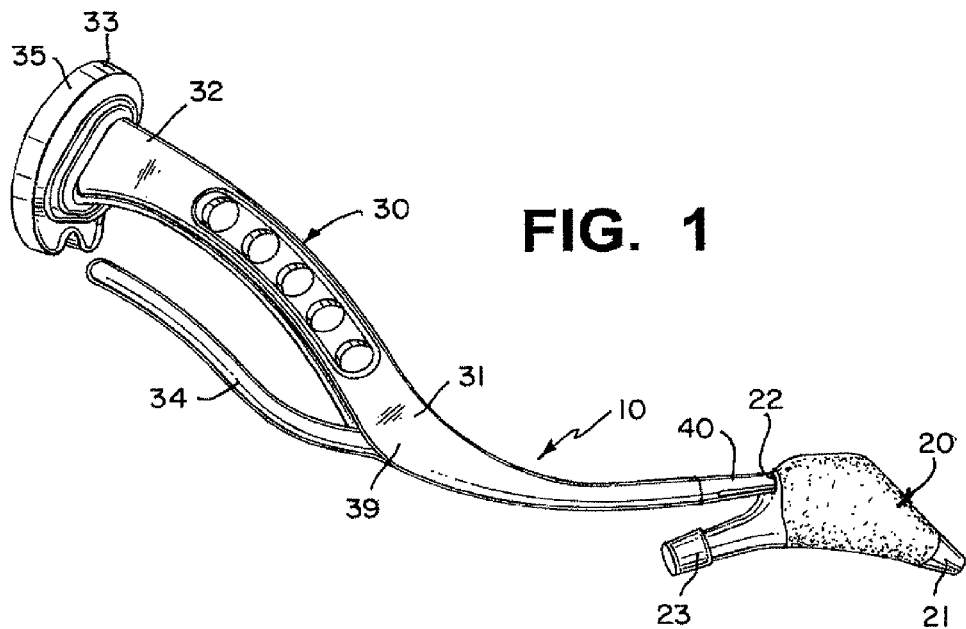
FIG. 1 shows a side view of a short hip implant engaged with a tool for assisting in the implant of the hip implant according to one embodiment of the invention.
Figure 3:
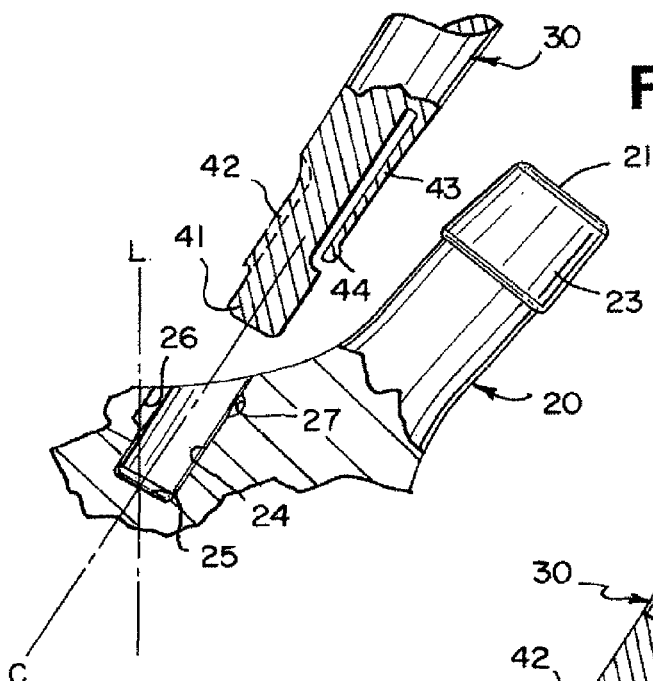
FIGS. 3A and 3B show a close-up view of the distal end of the tool of FIG. 1, respectively, disengaged and engaged with the proximal end of the implant of FIG. 2.
Figure 3:
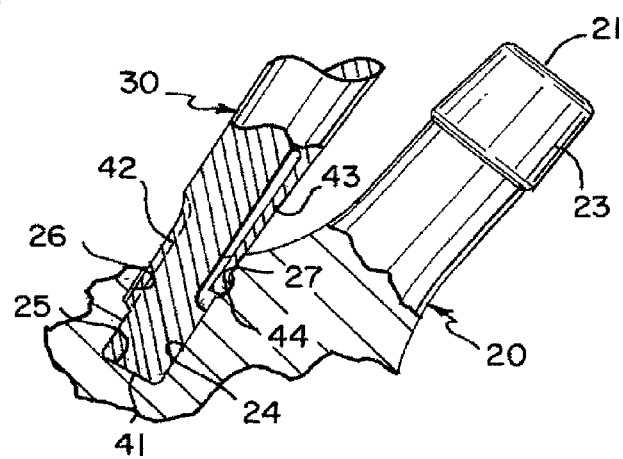

Referring to the drawings, FIG. 1 shows a hip implant system according to the invention, generally referred to as reference numeral 10. The hip implant system includes a short hip implant 20 and a tool 30 for assisting in the implantation of implant. Implant 20 includes a distal end 21, a proximal end 22, a stem 23 extending from proximal end 22, and an insertion cavity 24 formed in proximal end 22 (FIG. 3A). Tool 30 has a shaft 31, having a proximal end 32 and a distal end 40, a strike plate 33 connected to proximal end 32 and grip 34 extended from a medial portion 39 of shaft 31. Tool 30 is approximately 25 cm in length.

FIG. 1 depicts distal end 40 of tool 30 at least partially disposed in cavity 24 of implant 10. Distal end 40 is configured to mate with cavity 24 such that implant 10 may be securely held during the implant procedure, which as is described in more detail below, includes the steps of inserting and impacting via a "round the corner" surgical technique.

Figure 2:
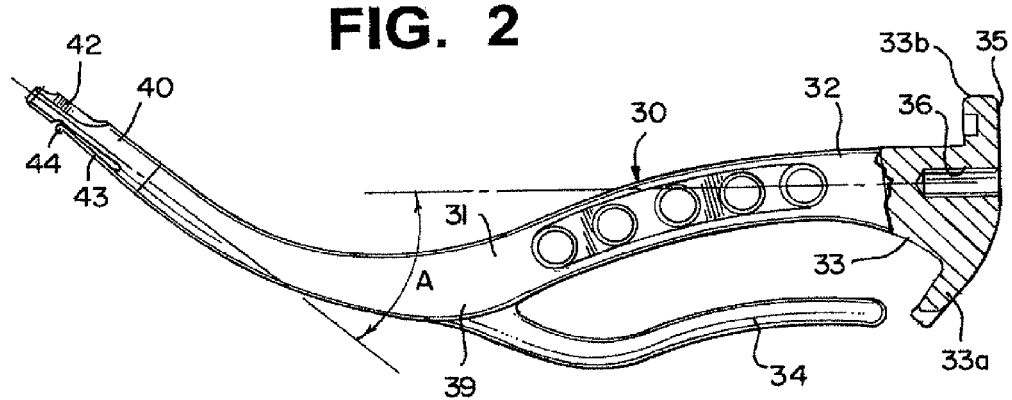
FIG. 2 shows a to scale, cross-sectional view of the tool of FIG. 1.

Referring to FIG. 2, tool 30 is shown in cross-section. A top surface 35 of strike plate 33 is rounded to permit plate 33 to be impacted at multiple locations as implant 10 is inserted into its ultimate position. As is described in greater detail below, the surgical technique for one embodiment of the invention requires a "round the corner" approach that permits the implant to be inserted while avoiding contact with the greater trochanter. To facilitate this requirement, strike plate 33 is rounded at a medial end 33a allowing impaction of implant 20 in a lateral direction at an oblique angle "around the corner" to a position inline with the axis of the femur. Further impaction can then be performed on a flat portion at lateral end 33b of plate 33 to seat implant 20 to the correct depth within the proximal femur.

Strike plate 33 has a counter-sunk bore 36 that extends from top surface 35 distally toward shaft 31 of tool 30. Bore 36 is configured to accept a portion of an alignment member 50 (FIG. 4). In a preferred embodiment, bore 36 is approximately 9 mm. The interface between tool 30 and alignment member 50 is preferably a clearance fit, which allows for easy operation of the alignment member and encourages intraoperative use of the alignment member, as its use consumes no additional time during surgery. The axis of bore 36 preferably is designed to be parallel with the implant axis when implant 10 is finally positioned in situ.

Grip 34 is fixed relative to shaft 31 and is shaped such that it complements the shape of the instrument body and provides the surgeon comfort and control when gripped during the method. Shaft 31 is preferably in the shape of an s-curve, so as to increase visualisation of the wound while clearing patient anatomy. That is, distal end 40 is not aligned with proximal portion 32 so as to provide the surgeon with a clear view of distal end 40 so as make the use of smaller incisions more practicable.

Referring to FIGS. 3A and 3B, the insertion feature is shown in detail in a disengaged position and an engaged position, respectively. Only the proximal portion 22 of implant 20 is depicted in FIGS. 3A and 3B. In accordance with the invention, cavity 24 has an axis C that is not aligned with the longitudinal axis L of implant 10. In a preferred embodiment, axis C is offset from longitudinal axis L by angle A, which ranges from 5 degrees to 55 degrees. More preferably, angle A ranges from 15 to 45 degrees. Most preferably angle A is about 40 degrees. Distal portion 25 of cavity 24 is preferably circular in cross section and preferably is approximately 9 mm in diameter. Cavity 24 includes a slot 26 that communicates with distal portion 25 and a dimple 27, each configured to accept features of insertion/impact tool 30. In a preferred embodiment, the distance from the center of dimple 27 to the bottom of cavity 24 is approximately 13 mm. Slot 26 is preferably 3.5 mm in width and need not run the full depth of the cavity.

Distal end 40 of tool 30 includes a distal tip 41 that is circular in cross-section and configured to engage distal portion 25 of cavity 24. Distal tip 41 is designed to transmit the impaction force from strike plate 33 to implant 20. Distal end 40 also includes a rib 42 which is configured to engage slot 26 of cavity 24. Rib 42 permits the surgeon to control the orientation of implant 10 as it permits implant 20 to have only one orientation with respect to insert/impactor tool 30 during operation. Distal end 40 also includes a cantilevered spring arm 43, which preferably extends from distal end 40 at a location circumferentially displaced from the location of rib 42. In a most preferred embodiment, rib 42 is located on the opposite side of distal end 40 from arm 43. Arm 43 includes a male feature or protrusion 44, which is preferably a spherical protrusion, designed to frictionally engage female feature or dimple 27 of implant 20. Frictional engagement of protrusion 44 with dimple 27 ensures that the implant remains attached while navigating through soft tissues. This design of attachment ensures that tool (or instrument) 30 is easily removed from implant 20 following final impaction. The spring arm 43 is designed so that at least one-quarter pound is required to be exerted to remove distal portion 40 from implant 20.

Referring to FIGS. 4 and 5A-5C, the described implant system allows the insertion of a short implant using the 'around the corner' surgical technique. The goal of this technique is to minimize the damage to the greater trochanter of the hip by broaching around the medial curve of the femur M and under the greater trochanter GT. The invention addresses the problem of greater trochanter impingement by both angling the insertion feature with respect to the long axis of the implant L and curving the impactor to travel around the greater trochanter GT during the "around the corner" insertion motion.

Figure 5:
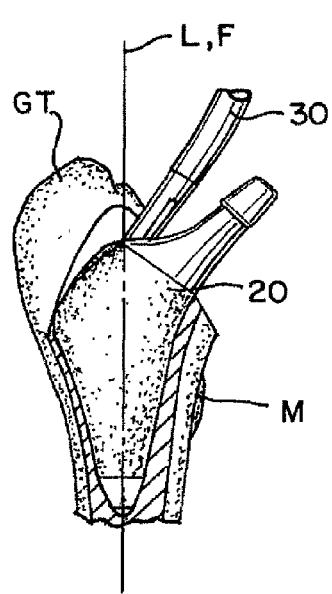
FIGS. 5A-5C show a schematic view of the implant being inserted into the femoral canal in three stages according to one embodiment of the invention.

System 10 is used as follows. The surgeon controls implant 20 with tool 30. Implant 20 is held in an engaged position with tool 30 by spring arm 43, which includes a male feature 44 that is disposed in a corresponding female feature 27 of implant 20. The surgeon controls the orientation of implant 20 by rib 42, which engages slot 26 of implant 20. Once a void is created in bone by broaching or another method known in the art, distal end 21 of implant 20 is positioned at the opening in the void. Referring to FIG. 5A, tool 30 can be engaged with implant 20 prior to or at this stage in the method.

When the surgeon desires to impact strike plate 33 to encourage implant 20 to assume the correct implant position, the surgeon engages distal end 40 of tool 30 with cavity 26 of implant 20. Referring to FIG. 5B, the surgeon then repeatedly impacts strike plate 33 at proximal end 32 of tool 30. As the surgeon impacts tool 30, implant 20 rotates about the medial curve of the femur M and under the greater trochanter GT as shown in FIGS. 5A-5C and in shadow FIG. 4. As implant 20 rotates, the longitudinal axis L of implant 20 rotates toward femoral axis F. The implant is correctly positioned when the longitudinal axis L of implant is substantially aligned with femoral axis F.

Referring to FIG. 4, once the surgeon believes that implant 20 has achieved its optimal position in the proximal femur, the position of implant 20 can be assessed by attaching alignment member 50 to tool 30 via the bore 36 in the plate 33. Member 50 includes a first arm 51 that engages with bore 36, a second arm 52 that extends at a right angle from first aim 51 and a third arm that extends at a right angle from second arm 52 in a direction parallel to first arm 51. In this way, third arm 53 can be aligned with the femoral axis of the leg to visually confirm that implant 20 is in the correct position. If implant 20 is misaligned, the surgeon can continue to impact plate 33 to correct the alignment or exert a torsional force on tool 30 to correct the varus/valgus orientation, e.g.

Removal of tool 30 from implant 20 is performed by pulling proximally on the proximal end of tool 30 with a force great enough to overcome spring arm 43. The force can be designed to range from one-quarter pound to five pounds. Excessive force is not required and as such the position of implant 20 in the proximal femur is not altered.

While the issue of navigating a short implant in a hip procedure is described in some detail herein, it is contemplated that the implant system can be used in any method where an implant needs to be inserted or positioned in a non-axial fashion. For example, a similar method and system can be used to implant humeral implants. Moreover, the invention is not necessarily limited to implantation of long-bone implants. The system can be employed wherever the insertion path of the implant benefits from being out of axis of the ultimate location of the implant.

System 10 of the invention, for example, can be used to navigate an implant to final position without impingement on defined bone feature or specific tissue structure that a surgeon wishes to spare, wherein the bone feature or specific tissue structure is located in a position that intersects an implant axis at a location proximal to the final position of the implant. Typically, in this situation, an implant would follow an axial path to its final position, one aligned with the implant axis. Utilizing the system of the invention, the surgeon can retain the bone feature that would otherwise need to be removed or at least damaged in providing a path for the implant, by inserting the implant along a non-axial path. In the preferred embodiment, implant 20 is navigated to a position wherein implant longitudinal axis L is aligned with femoral axis F, but the path taken is non-axial. That is, rather than delivering implant 20 by impacting implant 20 along an axis parallel (if not coincident) with implant axis L, implant 20 is impacted along a cavity axis C which is not parallel to implant longitudinal axis L. As a result, the path taken by implant 20 is curved rather than straight, and the greater trochanter bone, that would otherwise be sacrificed or at least damaged by contact with the implant if implant 20 took an axial path to its final position, is spared any damage. This same concept can be used to spare other bone features by the surgeon.

Specific construction details that are not shown are believed to be within the purview of those of ordinary skill in the art. The present invention has been described herein with reference to certain preferred embodiments. These embodiments are offered as illustrative, and not limiting, of the scope of the invention. Certain modifications or alterations may be apparent to those skilled in the art without departing from the scope of the invention, which is defined by the appended claims.

The invention claimed is:

1. A method of implanting an implant at least partially within a femur, the femur having a femoral axis, comprising the steps of:
   handling a system that includes:
      an implant comprising a body, the body having a proximal end, a distal end, a longitudinal axis and a cavity located at the proximal end, wherein the cavity defines a cavity axis that is not parallel to the longitudinal axis of the implant, and
      a tool for assisting in the implantation of the implant comprising a shaft having a distal end configured to mate with the cavity and a proximal end, the proximal end including a strike plate attached thereto;
   creating a void in the femur, the void being located medial of the greater trochanter;
   introducing the distal end of the implant into the void, whereat the longitudinal axis of the implant is not aligned with the femoral axis;
   engaging the distal end of the tool into the cavity of the implant;
   striking the strike plate to thereby rotate the longitudinal axis of the implant toward the femoral axis until the longitudinal axis of the implant is substantially aligned with the femoral axis; and
   disengaging the distal end of the tool from the cavity of the implant;
   wherein the implant has a stem extending from the proximal end, the stem extending from the femur when the implant is substantially aligned with the femoral axis; and
   wherein the stem is configured to receive a prosthetic femoral head.

2. The method of claim 1, wherein the handling step comprises handling a tool that has a distal portion that includes a cantilevered spring arm that extends from the distal portion, and the arm being configured to frictionally engage the cavity of the implant when at least partially disposed therein, and wherein the engaging step comprises engaging the arm with the cavity.

3. The method of claim 2, wherein the handling step comprises handling an implant that includes a dimple within the cavity, and handling a tool that includes a raised surface on a distal end of the cantilevered spring arm configured to at least partially engage the dimple when the distal end of the tool is engaged with the cavity, and wherein the engaging step comprises engaging the raised surface with the dimple.

4. The method of claim 3, wherein the cantilevered spring arm and the cavity of the implant are configured to permit disengagement of the tool and the implant when a force ranging from approximately one-quarter of a pound to five pounds is exerted proximally along the longitudinal axis of the tool.

5. The method of claim 2, wherein the creating step includes the step of creating a void by following a path around the medial curve of the femur and under the greater trochanter.

6. The method of claim 5, wherein the creating step includes the step of broaching around the medial curve of the femur and under the greater trochanter.

7. The method of claim 6, wherein the greater trochanter is substantially spared.

8. The method of claim 1, wherein the width of the implant increases from the distal end to the proximal end.

9. The method of claim 8, wherein the widest aspect of the implant is at least twice the width of the distal end of the implant.

10. The method of claim 1, wherein the implant has opposing sides that form at least a portion of the distal end, and the opposing sides diverge away from the longitudinal axis from the distal end.

* * * * *